US005962013A

United States Patent [19]
Wong et al.

[11] Patent Number: 5,962,013
[45] Date of Patent: *Oct. 5, 1999

[54] MONOLITHIC MATRIX TRANSDERMAL DELIVERY SYSTEM FOR ADMINISTERING MOLSIDOMINE

[75] Inventors: Ooi Wong, Fremont; Thuytien N. Nguyen, Hayward, both of Calif.

[73] Assignee: Cygnus, Inc., Redwood City, Calif.

[*] Notice: This patent is subject to a terminal disclaimer.

[21] Appl. No.: 09/128,909

[22] Filed: Aug. 4, 1998

Related U.S. Application Data

[63] Continuation of application No. 08/581,531, filed as application No. PCT/US94/07544, Jul. 6, 1994, Pat. No. 5,804,214, which is a continuation-in-part of application No. 08/088,877, Jul. 8, 1993, abandoned.

[51] Int. Cl.$^6$ ....................................................... A61F 13/02
[52] U.S. Cl. ............................ 424/448; 424/445; 424/449
[58] Field of Search ..................................... 424/448, 449, 424/445

[56] References Cited

U.S. PATENT DOCUMENTS

| | | |
|---|---|---|
| 3,598,122 | 8/1971 | Zaffaroni . |
| 4,087,539 | 5/1978 | Muchowski et al. . |
| 4,089,969 | 5/1978 | Muchowski et al. . |
| 4,097,579 | 6/1978 | Muchowski et al. . |
| 4,140,698 | 2/1979 | Van Horn et al. . |
| 4,232,038 | 11/1980 | Kluge et al. . |
| 4,344,943 | 8/1982 | Muchowski . |
| 4,347,185 | 8/1982 | Muchowski et al. . |
| 4,347,186 | 8/1982 | Muchowski et al. . |
| 4,347,187 | 8/1982 | Muchowski et al. . |
| 4,353,829 | 10/1982 | Thurber et al. . |
| 4,397,862 | 8/1983 | Mroszczak et al. . |
| 4,454,151 | 6/1984 | Waterbury . |
| 4,454,326 | 6/1984 | Muchowski et al. . |
| 4,456,759 | 6/1984 | Muchowski et al. . |
| 4,457,941 | 7/1984 | Ringold et al. . |
| 4,458,081 | 7/1984 | Muchowski et al. . |
| 4,490,322 | 12/1984 | Zierenberg . |
| 4,496,741 | 1/1985 | Doherty . |
| 4,505,927 | 3/1985 | Muchowski et al. . |
| 4,564,010 | 1/1986 | Coughlan et al. . |
| 4,568,343 | 2/1986 | Leeper et al. . |
| 4,751,087 | 6/1988 | Wick . |
| 4,780,320 | 10/1988 | Baker . |
| 4,873,340 | 10/1989 | Muchowski et al. . |
| 4,874,871 | 10/1989 | Fleming et al. . |
| 4,919,939 | 4/1990 | Baker . |
| 4,956,171 | 9/1990 | Chang . |
| 4,988,822 | 1/1991 | Muchowski et al. . |
| 4,994,267 | 2/1991 | Sablotsky . |
| 5,091,182 | 2/1992 | Ong et al. . |
| 5,149,538 | 9/1992 | Granger et al. . |
| 5,308,625 | 5/1994 | Wong et al. . |
| 5,358,715 | 10/1994 | Wong et al. . |
| 5,589,498 | 12/1996 | Mohr et al. . |

FOREIGN PATENT DOCUMENTS

| | | |
|---|---|---|
| 0 127 468 | 12/1984 | European Pat. Off. . |
| 0 319 988 | 6/1989 | European Pat. Off. . |
| 0 371 496 | 6/1990 | European Pat. Off. . |
| 0 399 432 | 11/1990 | European Pat. Off. . |
| 0 481 443 | 4/1992 | European Pat. Off. . |
| 3843238 | 2/1990 | Germany . |
| 3843239 | 2/1990 | Germany . |
| WO 86/06281 | 11/1986 | WIPO . |

OTHER PUBLICATIONS

Guzman et al., "Absolute configuration of 5–benzoyl–1, 2–dihydro–3H–pyrrolo [12–a]pyrrole–1–carboxylic–acid, the active enantiomer of ketorolac" J. Med. Chem. (1986) 29:589–591.

(List continued on next page.)

*Primary Examiner*—D. Gabrielle Brouillette
*Attorney, Agent, or Firm*—Angela P. Horne; Barbara G. McClung

[57] ABSTRACT

This invention provides monolithic matrix formulations for transdermal administration of molsidomine. The device includes a copolymer of 2-ethylhexyl acrylate, 2-hydroxyethylmethacrylate, and methacrylic acid. The invention also provides transdermal devices having a monolithic matrix made using such a formulation in combination with an active ingredient and a vehicle or vehicle formulation.

21 Claims, 1 Drawing Sheet

OTHER PUBLICATIONS

Muchowski et al., "Synthesis and antiinflammatory and analgesic activity of 5–aroyl–1,2–dihydro–3H–pyrrolo[1,2–a]pyrrole–1–carboxylic–acids and related compounds" J. Med. Chem. (1985) 28:1037–1049.

Gu et al., "Light degradation of ketorolac tromethamine" Int. J. Pharm. (1988) 41:105–113.

Gu et al., "Kinetics and mechanisms of the autoxidation of ketorolac tromethamine in aqueous solution" Int. J. Pharm. (1988) 41:95–104.

Yu et al., "Percutaneous absorptionof nicardipine and ketorolac in rhesus monkeys" Pharm. Res. (1988) 5(7):457–462.

Buckley et al., "Keterolac–a review of its pharmacodynamic and pharmacokinetic properties, and therapeutic potential" Drugs (1990) 39:86–109.

Yamada et al., "Mechanismof enhancement of percutaneous absorption of molsidomine by oleic acid" Chem. Pharm. Bull. (1987) 35:3399–3406.

Merck Index, 10th edition, "Molsidomine" (1983) 6087:892.

Asahi et al., "Chemical and kinetic study on stabilities of 3–morpholinosydnonimine and its N–ethoxycarbonyl derivative" Chem. Pharm. BUll. (1971) 19:1079–1088.

Kukovetz et al., "Mechanism of vasodilation by molsidomine" Am. Heart J. (1985) 109:637–640.

Yamada et al., "Enhancement of percutaneous absorption of molsidomine" Chem. Pharm. Bull. (1987) 35(8):3390–3998.

Ostrowski et al., "Pharmacokinetics of molsidomine in humans" Am. Heart J. (1985) 109:641–643.

Alza Corporation Newsletter "Alza pioneers work in trans-dermal delivery" (1991) 4(1):1–4.

Andrews et al., "Fentanyl–a review" Clin. Anaesthiol. (1983) 1(1):97–122.

Bickers et al., "Epidermis: A site of drug metabolism in neonatal rat skin" Pharmacol. (1982) 21:239–247.

Bucks, "Skin structure and metabolism: Relevance to the design of cutaneous therapeutics" Pharm. Res. (1984) 1:148–153.

Bromage, "The price of intraspinal narcotic analgesia: basic constraints" Anesthesi and Analgesia (1981) 60(7):461–463.

Casale et al., "Induction of human cutaneous mast cell degranulation by opiates nad endogenous opioid peptides: Evidence for opiate and nonopiate receptor participation" J. Aller. Clin. Immunol. (1984) pp. 775–781.

Diebschlag et al., "A double–blind study of the efficacy of topical ketorolac tromethamine gel in the treatment of ankle sprain in comparison to placebo ad etofenamate" J. Clin. Pharmacol. (1990) 30(1):82–89.

Finch et al., "Clinical investigation of the analgesic potency and respiratory depressant activity of fentanyl, a new narcotic analgesic" J. Clin. Pharmacol. (1967) 7(1):46–51.

Fjellner et al., "Potentiation of histamine–induced itch and flare responces in human skin by the enkephalin analogue FK33–824, J–endorphin and morphine" Arch. Derm. Res. (1982) 274:29–37.

TGrosman, "Histamine release from human basophils and isolated rat mast C induced by ketobemidone, pethidine and the spasmolytic A29" Acta Pharmacol. et Toxicol. (1982)50:78–80.

Hermens et al., "Comparison of histamine release in human skin mast cells induced by morphine, fentanyl, and oxymorphine" Anesthesiology (1985) 62:124–129.

Liaw et al., "Percutaneous absorption of ketorolac topical gel formulations vehicle effects and in–vitro–in–vivo correlations" J. Pharm. Sci. (1987) 76(11):S280.

Menardo et al., "Skin test reactivity in infancy" Aller. Clin. Immunol. (1985) 75(6):646–651.

Martin et al., "Sensitization by in vitro incubation with morphine of the myenteric plexus–longitudinal msucle preparation" J. Pharmacol. (1982) 13(1):3–10.

Palestine et al., "Skin manifestations of pentazocine abuse" Am. Acad. Dermatol. (1980) 2(1):47–55.

Philbin et al., "Histamine release with intravenous narcotics: Protective effects of H1 and H1–receptor antagonists" Klin. Wochenschr. (1982) 60:1056–1059.

Ponte, "A suspected case of codeine–induced erythema mutli–forme" Drug Intelligence and Clinical Pharmacy (1983) 17:128–130.

Reiz et al., "Side–effects of epidural morphine" Lancet (Jul. 26, 1980) 2:203–204.

Roy et al., "Concepts in transdermal delivery of narcotics II: In vivo permeation of suffentanil and fentanyl through human skin" Pharm. Res. (1986) 3(5):54S (Abstract No. 60).

Saucedo et al., "Morphine–induced skin wheals: A possible model for the study of histamine release" Clin. Pharmacol. Ther. (1985) 38(4):365–370.

Schnur, "Morphine tolerance and sensitization in the hamster" Pharmacol. Biochem. & Behav. (1985) 22:157–158.

Shipton, "Pruritus–a side effect of epidural fentanyl for postoperative analgesia" SA Med. J. (1984) 66:61–62.

Wang et al., "Suppressive effects of oral ketotifen on skin responses to histamine, codeine, and allergen skin tests" Ann. Aller. (1985) 55:57–61.

Wilham et al., "Concepts in transdermal delivery of narcotics I: Enzymatic activity in hairless mouse skin and human epidermal homogenates" Pharm. Res. (1986) 3(5):54S (Abstract No. 59).

Wong et al., "A randomized double–blind evaluation of ketorolac tromethamine for postoperative analgesia in ambulatory surgery patients" Anesthesiology (1993) 78(1):6–14.

Wong et al., "An evaluation of ketorolac as sole analgesic after outpatient surgery" ANesthesiology (1972) 77(Supplement3A):A6.

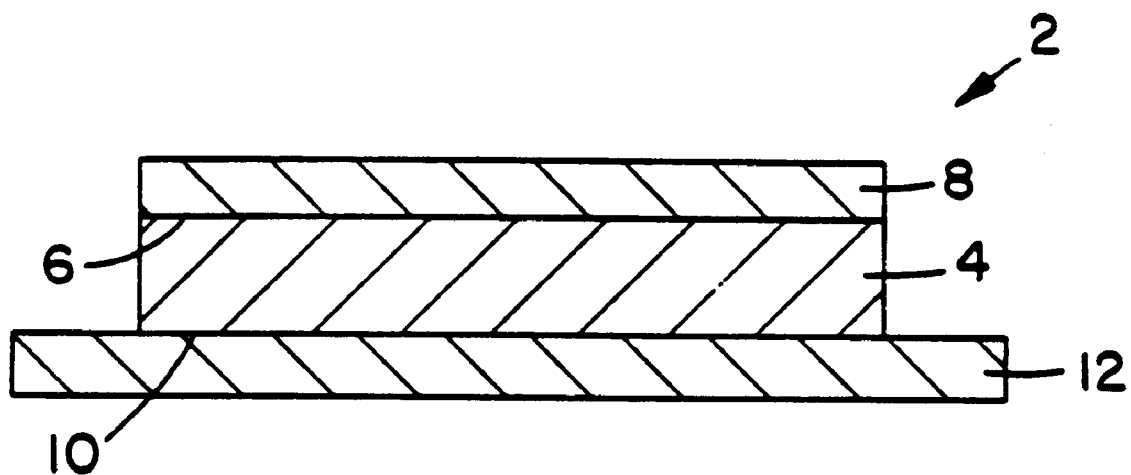

MONOLITHIC MATRIX TRANSDERMAL DELIVERY SYSTEM FOR ADMINISTERING MOLSIDOMINE

This application is a continuation of U.S. application Ser. No. 08/581,531 filed Mar. 7, 1996, now U.S. Pat. No. 5,804,214, which is a national stage application filed under 35 U.S.C. §371(b) of PCT international application number PCT/US94/07544, filed Jul. 6, 1994, which in turn is a continuation-in-part of U.S. application Ser. No. 08/088,877, filed Jul. 8, 1993, now abandoned, from which application priority is claimed pursuant to 35 U.S.C. §120 and which is incorporated herein by reference in its entirety.

BACKGROUND OF THE DISCLOSURE

1. Technical Field

This invention relates to transdermal drug delivery.

2. Background Art

1. Monolithic Matrix Delivery Devices

Transdermal delivery has become an increasingly acceptable mode for administration of prescription and nonprescription drugs, and considerable effort has been expended toward development of transdermal drug delivery systems. A number of drugs have reached the market in transdermal delivery form, most popularly in the form of an adhesive patch.

Essentially, the methodology of transdermal drug delivery involves placing the drug on the skin surface and allowing the drug to permeate through the skin. Transdermal delivery devices employ a structure that serves as a reservoir for the drug and that provides for bringing the drug into diffusive communication with the skin surface. In one general type, the structure includes a three-dimensionally stable matrix material having a discrete size and shape; such a structure may be referred to as a "monolithic matrix".

A variety of monolithic matrix formulations have been proposed for use in transdermal delivery systems.

U.S. Pat. No. 5,149,538 describes transdermal delivery of opioids using an adhesive matrix prepared from polymers and copolymers of acrylic esters or methacrylic esters and copolymers of acrylic esters or methacrylic esters and other ethylenically-unsaturated monomers. Preferred acrylic adhesives are butyl acrylate, ethyl acrylate, ethyl hexyl acrylate, vinylacetate/ethylene acrylate and mixtures of these.

U.S. Pat. No. 4,956,171 describes using sucrose cocoate and methyl laurate for permeation enhancement in transdermal delivery of buprenorphine HCl or hydromorphone HCl, in an adhesive matrix made up of polyacrylic polymers or vinyl acetate-acrylic polymers, and, particularly, a vinyl acetate-acrylic multipolymer solution marketed by Montsanto Co. under the name Gelva® 788.

German Patent Publications DE 38 43 239 and DE 38 43 238 describe transdermal delivery of physostigmine using a polymer matrix made up, in one example, of an acrylate copolymer of 2-ethylhexyl acrylate, vinyl acetate, and acrylic acid; a methacrylate copolymer of dimethylaminoethyl methacrylate and neutral methacrylic acid esters; and a triglyceride of capryl/caprinacids.

International Application No. PCT/US86/00789 (WO 86/06281) describes a pressure-sensitive adhesive tape for transdermal delivery of nitroglycerin, having a pressure-sensitive adhesive coating made up of an acrylic adhesive copolymer including as a major constituent a hydrophobic monomeric acrylic or methacrylic acid ester of a $C_{4-10}$ alkyl alcohol; and including a reinforcing monomer selected from acrylic acid, methacrylic acid, $C_{1-3}$ alkyl acrylate or methacrylate, acrylamide, methacrylamide, t-butyl acrylamide, diacetone acrylamide, vinyl ether, substituted ethylene, and vinyl ester.

European Patent Publication No. EP 0 481 443 A1 describes a transdermal delivery system having a polymeric matrix made up of a acrylic polymer 7927 79 Röhm-Pharma.

2. Ketorolac Tromethamine

Ketorolac is a pyrrolizine carboxylic acid derivative. Combined with tromethamine, ketorolac forms a salts ("ketorolac tromethamine"), which was greater aqueous solubility than ketorolac. The chemical structure of ketorolac and ketorolac tromethamine are shown below:

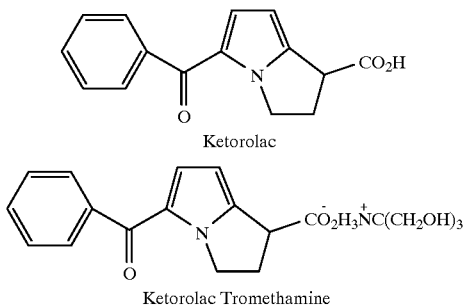

Ketorolac

Ketorolac Tromethamine

Ketorolac tromethamine is a nonsteroidal anti-inflammatory drug useful for short-term management of moderate to severe pain. Ketorolac tromethamine is available via prescription in oral tablet form (10 mg strength) and in intramuscular injection form (30 mg/ml).

Ketorolac tromethamine has a chiral center and is used as a racemate marketed under the name Toradol; the (−)-S isomer has many times greater analgesic potency than the (+)-R isomer (A. Guzman et al., 1986). Ketorolac tromethamine is an off-white crystalline powder and has a $pK_a$ value of 3.49. Ketorolac is quite lipophilic with a long PC (partition coefficient) value of 2.72 (Muchowski et al., 1985). Ketorolac tromethamine is extremely stable in aqueous solutions at pH 4–8, with a very long shelf-life at 25° C. (L. Gu et al., 1988 a); however, it is light sensitive with decarboxylation, especially in the presence of oxygen (L. Gu et al., 1988 b), and ketorolac solutions should be protected from light exposure. The free acid of ketorolac in methanol exhibits UV absorption maxima at 245 nm and 312 nm, with molar absorptivities of 7080 and 17400, respectively (Franco et al. 1982).

Solubility of ketorolac tromethamine in various vehicle systems has been measured by Yu et al. (1988). Certain of the solubilities are given below.

| Vehicles | Solubilities (mg/ml) |
| --- | --- |
| water | 725 |
| propylene glycol (PG) | 200 |
| PG (50%), Oleic acid (50%) | 110 |

The analgesic property of ketorolac tromethamine, like that of other nonsteroidal anti-inflammatory drugs, appears to result from cyclo-oxygenase inhibition by way of action on inhibition of prostaglandin synthesis (Buckley et al. (1990)). Ketorolac tromethamine has high analgesic and anti-inflammatory potency; administered orally, the analgesic potency of ketorolac tromethamine is about 3–6 times that of indomethacin, about 25–50 times that of naproxen, and about 180 times that of aspririn, and the antiinflammatory potency of ketorolac tromethamine is about 2–3 times that of indomethacin or naproxen.

Yu et al. (1988) describes percutaneous absorption of ketorolac and ketorolac tromethamine in Rhesus monkeys using a number of solution formulations. Two vehicle combinations (propylene glycol and linoleic acid, and propylene glycl and oleic acid) were shown to be effective in enhancing percutaneous absorption of both ketorolac and ketorolac tromethamine. High $C_{max}$ values were achieved within 8 hours.

3. Molsidomine

Molsidomine is a vasodilator, useful for example in treatment of angina pectoris.

Molsidomine (N-5-ethoxycarbonyl-3-morpholinosydnonimine) is a sydnonimine derivative having a mesoionic aromatic ring. It is also an ester prodrug. Its chemical structure is shown below:

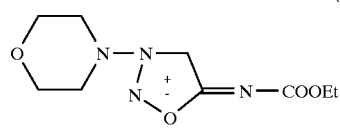

(Molsidomine)

Molsidomine is a white colorless crystal powder, practically tasteless or odorless. The imine has a molecular weight of 242 with a melting point of 140–141° C. and a $pK_a$ value of 3.34 at 25° C. It exhibits a UV absorption maximum at 326 nm in $CHCl_3$. The solubilities (saturated) of molsidomine in various solvent systems, as reported in Yamada et al. (1987), *Chem. Pharm. Bull.*, Vol. 35, pp. 3399–406, are shown below:

| Vehicles | Solubilities at 25° C. (%) |
| --- | --- |
| Glycol salicylate | 15.1 |
| Propylene glycol | 6.37 |
| PEG 400 | 5.23 |
| Glycerin | 1.80 |
| Oleic Acid | 1.37 |
| Octyl.decyl oil | 0.36 |
| Isopropyl myristate | 0.09 |

Molsidomine is shown to be freely soluble in $CHCl_3$; soluble in dilute HCl, ethanol, ethyl acetate, methanol; sparingly soluble in water, acetone, benzene; very slightly soluble in ether, petroleum ether, Merck Index, $10^{th}$ edition, page 892 (1983). It is soluble in propylene glycl and a variety of organic solvents. The chemical stability of molsidomine has been investigated in detail by Asahi et at. (1971), *Chem. & Pharm. Bull.*, Vol. 19, pp. 1079–88, as shown below.

| pH | $t_{90}$ (days) at 20° C. |
| --- | --- |
| 1–2 | 38 |
| 4 | 250 |
| 5–7 | 950 (2.6 years) |
| 10 | 400 |
| 11 | 40 |

Molsidomine is photosensitive, particularly in sunlight.

Molsidomine has been shown to process a sustained anti-anginal effect and can be metabolized to SIN-1, which is readily converted into the active metabolite SIN-1A (carries a free nitroso group).

A very recent investigation on the vasodilation action of molsidomine and other vasodilators, including nitroglycerine reveals that it is the nitric oxide, liberated from the active metabolite SIN-1A, that activates the soluble guanylate cyclase, which in turn causes vasodilation. This is a major difference from the vasodilation action of nitroglycerin.

The coronary vasodilation action of nitroglycerine depends on the presence of cysteine. Cysteine deficiency was found to be associated with the tolerance developed for nitroglycerin uses. After prolonged exposure to nitroglycerin, tolerance toward the drug developed in coronary strips can be antagonized by cysteine. However, the active metabolite of molsidomine. SIN-1A, is active in both the presence and the absence of cysteine; therefore, molsidomine produces insignificant tolerance (Kulovetz et al. (1985), making it a better alternative for anti-anginal therapy.

In in vivo studies of transdermal delivery of molsidomine in rats, a combination of propylene glycol with 10% oleic acid produced an estimated flux of 399 $\mu g/hr\text{-}cm^2$ for molsidomine (Yamada et al. (1987) *Chem. Pharm. Bull.*, Vol. 35(8), pp. 3390–98).

A single oral dose of 2 mg of molsidomine can produce anti-anginal effects in patients with coronary heart disease for 3 to 5 hours (J. Ostrowski et al. (1985) *Am. Heart Jour.*, pp. 641–43). Different oral dosing levels can benefit patients having different degrees of coronary heart disease. Typically, oral doses of 2 mg three times daily, or 4 mg four times daily are suggested. Pharmacokinetic data indicate that the total clearance and peak plasma concentration of molsidomine were 46,000 ml/hr and 15 mg/ml, respectively, following administration of an oral dose of 2 mg. The bioavailability of molsidomine from oral doses is 44%. Generally, the effective blood concentration of a drug is less than the peak plasma concentration; therefore an estimation of target flux based on the effective blood concentration should be a better indication of the delivery rate required to produce therapeutic response.

European Patent Publication No. EP 0 127 468 A1 describes percutaneous formations containing various amounts of molsidomine and various absorption promoters.

SUMMARY OF THE INVENTION

We have discovered that certain monolithic acrylic matrix formulations can be effective in transdermal delivery of active agents. By way of examples, we have discovered that ketorolac tromethamine and molsidomine can be effectively delivered transdermally using monolithic acrylic latex matrix formulations according to the invention; particularly, using an accepted in vitro model we have demonstrated transdermal delivery of ketorolac tromethamine and of molsidomine from the monolithic acrylic latex matrix compositions of the invention at skin flux rates suitable for therapeutic use. The acrylic latex matrix formulations of the invention have low skin irritation scores.

DISCLOSURE OF THE INVENTION

Accordingly, in one general aspect the invention features a monolithic matrix formulation for transdermal administration of an active agent, which formulation includes in combination as a copolymer 2-ethylhexyl acrylate, 2-hydroxyethyl methacrylate, and methacrylic acid; and transdermal delivery devices that include such a monolithic matrix formulation.

A "monolithic matrix", as that term is used herein, is the material, typically in the form of a firm or gel, in a transdermal drug delivery system that contains the active agent to be delivered and a vehicle or vehicle combination, which may include an enhancer, and from which the active agent passes. A "monolithic matrix formulation", as that term is used herein, is the combination of components used to form a monolithic matrix.

In preferred such embodiments the monolithic matrix formulation includes as a copolymer the following:

| 2-ethylhexyl acrylate | 60–95 wt. % |
|---|---|
| 2-hydroxyethyl methacrylate | 5–25 wt. % |
| methacrylic acid | 0.5–10 wt. % |

In some embodiments, the monolithic matrix formulation includes as a copolymer 2-ethylhexyl acrylate, 2-hydroxyethyl methacrylate, methacrylic acid and acrylic acid. In preferred such embodiments the monolithic matrix formulation includes as a copolymer the following monomers:

| 2-ethylhexyl acrylate | 60–98 wt. % |
|---|---|
| 2-hydroxyethyl methacrylate | 0.1–5 wt. % |
| methacrylic acid | 0.5–10 wt. % |
| acrylic acid | 0.5–10 wt. % |

In another general aspect the invention a monolithic matrix formulation for transdermal administration of an active agent, which formulation includes a composition selected from the group consisting of AE 2390 and AE 2616; and transdermal delivery devices that include such a monolithic matrix formulation.

In another general aspect the invention features a method for making a monolithic matrix for transdermal delivery of an active agent, including steps of combining the active agent with a selected vehicle or vehicle composition and with the matrix formulation; spreading the resulting material, containing active agent and matrix formulation homogeneously dissolved, dispersed, or suspended in the vehicle, to form a film, and drying the matrix film.

In some embodiments for administration of ketorolac tromethamine, and in some embodiments for administration of molsidomine, the vehicle includes propylene glycol monolaurate ("PGML") or propylene glycol ("PG") or, more preferably, includes a combination of PGML and PG. The method for making the monolithic matrix for such embodiments includes steps of mixing the active agent with the vehicle, and stirring and warming the mixture; adding the components of the monolithic matrix formulation; stirring and mixing resulting material thoroughly to form a homogeneous suspension, dispersion, or solution; spreading the homogeneous material evenly onto a release liner to form a film; and drying the film.

Transdermal delivery devices according to the invention include, in some embodiments, a backing layer, serving to support the monolithic matrix film during manufacture and storage, and while the device is in use; and a removable release liner, serving during storage to protect those portions of the device that are in contact with the skin when the device is in use.

In another general aspect the invention features a method for administration of an active agent to a subject, including steps of providing a monolithic matrix formulation including in combination as a copolymer 2-ethylhexyl acrylate, 2-hydroxyethyl methacrylate, and methacrylic acid and, in some embodiments additionally acrylic acid; and contacting the active agent-containing monolithic matrix formulation with the subject's skin.

In some embodiments, the active agent is ketorolac tromethamine, and the method includes providing a monolithic matrix according to the invention, containing an effective amount of ketorolac tromethamine; in other embodiments, the active agent is molsidomine, and the method includes providing a monolithic matrix according to the invention, containing an effective amount of molsidomine.

DESCRIPTION OF PREFERRED EMBODIMENTS

Preferred embodiments of the invention will now be described, beginning with a brief description of the drawing.

BRIEF DESCRIPTION OF THE DRAWING

The FIGURE is a sketch showing a transdermal delivery device including a monolithic matrix according to the invention.

MODES OF CARRYING OUT THE INVENTION

Fabrication of Monolithic Matrices

Generally, acrylic latex matrix formulations according to the invention are made by suspending or dissolving or dispersing the active agent in a selected vehicle or vehicle composition and mixing with a selected polymer system to form a homogeneous solution, suspension, or dispersion. The resulting material, containing active agent and polymer system homogeneously dissolved or suspended in the vehicle, is spread into a film and dried. The resulting active agent-containing monolithic matrix film can then be stored until use.

Preferably, the material is spread onto a backing layer of a release liner, typically a polymer film, and the film is covered after drying with an additional release liner and stored in a water-impermeable enclosure. With reference now to the FIGURE, in which a transdermal delivery device according to the invention is shown in transverse section generally at 2, the monolithic matrix film constitutes matrix layer 4, which is affixed to a surface 6 of backing layer 8. The matrix layer 4 contains the active agent to be delivered. When the device is in use on a patient, a surface 10 of matrix layer 4 contacts the surface of the patient's skin, and the active agent passes from the matrix layer at a surface 10 onto and through the skin; when the device is in storage, the matrix layer is protected by peelable release liner 12.

As noted above, certain commercially available polymer systems can be suitable for use in constructing monolithic matrices according to the invention. Alternatively, the selected polymer system can be constructed as a copolymer from its monomer constituents according to copolymerization techniques well known in the polymer art. Particularly, in some embodiments the copolymer is a random copolymer formed by emulsion polymerization beginning with the subunits. The resulting polymer system can be provided in emulsion form.

Use

The monolithic matrix formulations according to the invention can be used in the construction of monolithic matrix transdermal delivery devices for administration of any of a variety of active agents. For use, the matrix, containing the active agent and, preferably, supported on a backing layer, is brought into contact with the subject's skin. The active agent then passes from the matrix into and through the skin.

The monolithic matrix formulations of the invention will now be illustrated by showing the construction and operation of transdermal delivery matrices capable of delivering, by way of examples, molsidomine and ketorolac tromethamine, at skin flux rates suitable for therapeutic use. Other active substances can be effectively transdermally delivered using monolithic matrices according to the invention, including substances that do not pass readily through the skin.

EXAMPLE A

Monolithic Matrix Formulations for Delivery of Ketorolac Tromethamine

By way of example, monolithic matrices containing ketorolac tromethamine and having acrylic latex matrix formulations according to the invention were made, and their delivery rates were demonstrated in an in vitro model system.

Generally, the protocol was as follows. An appropriate amount of a combination of the selected vehicle components was weighed into a vial containing a ketorolac tromethamine residue. The vial was warmed and the mixture was stirred to dissolve or suspend the ketorolac tromethamine in the vehicle, and then the components of the selected polymer system were weighed into the vial. The resulting mixture was then mixed using a rotary mixer for a time sufficient to form a homogeneous solution, or suspension, or dispersion of the components, typically at least 1 or 2 hours. The homogeneously mixed wet material was then spread evenly using a Gardner knife onto the backing layer of a release liner (usually a polyethylene plastic sheet) to make a film having a suitable thickness, typically between 20 and 50 mils when wet. Where an organic solvent was used in the mixing steps, the film was allowed to dry on the backing sheet in a hood for a time, typically at least 20 minutes, and then was further dried for a time in an oven at an elevated temperature, typically 1 to 3 hours at about 70° C., to form a cured film affixed to the backing sheet. Thereafter the film was cooled to room temperature, a release liner was used to cover the exposed film surface and the film was stored in a plastic bag until use.

More particularly, the following protocol was used to make ketorolac tromethamine-containing monolithic matrices having acrylic latex matrix formulations according to the invention for prototype demonstrations, using an accepted in vitro model, of delivery of ketorolac tromethamine.

1. Target Flux of Ketorolac

It is necessary to combine both the oral dose and the pharmacokinetics data to estimate the target flux of ketorolac. For an oral dosage regimen of ketorolac tromethamine, it is recommended that 10 mg be given every 6 hours as needed for short-term management of moderate to severe pain.

High oral bioavailability of 80–100% has been determined for ketorolac tromethamine. Following an oral administration of 10 mg of ketorolac, the $C_{max}$ of about 0.8 µg/ml was rapidly attained. The total clearance of ketorolac is 1750 ml/hr/70 kg. From the mean plasma concentration/time profiles of ketorolac after oral administration of 10 mg of ketorolac tromethamine, at the 6 hour time points, the plasma concentration is approximately 0.2 to 0.3 µg/ml (Jung et al. (1988), (Jallad et al. (1990), (Mroszczak (1990). The Maintenance Target Flux is therefore estimated to be in the range of 26 to 40 µg/hr/cm². As the total clearance and the volume of distribution (7.7 lit/70 kg) are small, the Loading Dose of ketorolac tromethamine may not present a problem for reaching the maintaining target flux.

2. Materials

Ketorolac tromethamine injectables (Toradol) of 60 mg/2 ml were purchased from a local pharmacy. The injectables contain 10% ethanol and sodium chloride adjusted to isotonic conditions. The injectables were adjusted to physiological pH using either HCl or NaOH. Propylene glycol monolaurate ("PGML") used in the skin permeation studies was obtained from Gattefosse (Elsmford, N.Y.) Morstik 607 was obtained from Morton-Thiokol, Silicone 2920 from Dow Corning, and Gelva 2333 from Monsanto. Precoated thin layer chromatography (t.l.c.) plates, obtained from Analtech, were Silica Gel GF with a thickness of 250 microns. Other chemicals used were reagent grades.

Acrylics AE 2616, AE 271, AE 1201 and AE 2390 were obtained from Avery Dennison Chemical Division, Mill Hall, Pa. The compositions of AE 2390 and of AE 2616 are reported by Avery as follows:

| AE 2390 | |
|---|---|
| 2-ethylhexyl acrylate (CAS # 103-11-7) | 60–98 wt. % |
| 2-hydroxyethyl methacrylate (CAS # 868-77-9) | 0.1–5 wt. % |
| methacrylic acid (CAS # 79-41-4) | 0.5–10 wt. % |
| acrylic acid (CAS # 79-10-7) | 0.5–10 wt. % |
| AF 2616 | |
| 2-ethylhexyl acrylate (CAS # 103-11-7) | 60–95 wt. % |
| 2-hydroxyethyl methacrylate (CAS # 868-77-9) | 5–25 wt. % |
| methacrylic acid (CAS # 79-41-4) | 0.5–10 wt. % |

3. Fabrication of Monolithic Matrices

An appropriate amount of the vehicle combination (PGML, PG) was weighed into the vial containing the ketorolac tromethamine residue. The vial was warmed, and the mixture was stirred into solution or suspension before the appropriate polymer system was weighed into the vial. Each formulation was then mixed with a rotary mixer for at least 1–2 hours until it formed a homogeneous solution or suspension. The material was spread evenly with a Gardner knife on the backing layer of a release liner such as a polyethylene plastic sheet to make films of various thickness, in the range 20–50 mils (wet). If an organic solvent was involved, the film was allowed to dry in a hood for at least 20 minutes and then further dried in an oven at 70° C. for 1 to 3 hours. After cooling the cured films, a release liner was used to cover the films and they were stored in plastic bags until use.

4. Skin Flux Text

Human cadaver epidermis was removed carefully from dermatoned full thickness skin after the skin had been heated in deionized water at 60° C. for one to two minutes. The stripped epidermis was placed between two polyethylene plastic sheets and refrigerated at –20° C. until use. Discs of the epidermis having a diameter of ⅝" were punched out with a die and tested for leakage by soaking the epidermis in water, then spreading it flat on a plastic sheet, and pressing the top of the epidermis lightly a few times with a piece of laboratory tissue. Leakage of the epidermis was detected by appearance of wet spots on the tissue.

Epidermis discs proving to be free of leaks were placed on top of a receiver cell of a modified Franz vertical diffusion cell assembly, and a donor cell was placed on top of the receiver cell. A small magnetic stir bar was inserted through the sampling port into the donor cell compartment. The diffusion cell assemblies were clamped together and transferred to a skin permeation room (controlled at 32° C.) The receiver cell compartments were filled with 8.0 ml of isotonic phosphate buffer, pH 7.0.

For tests of solution formulations, a volume of 0.2 ml of a selected liquid formulation was applied to the donor cell compartments, which were then sealed using a Teflon plug. For matrix formulations, appropriately sized matrix discs having a diameter of ⅝" were punched with a die. The release liner was removed and the matrix was placed onto the epidermis before the diffusion cell assembly was clamped together. At the appropriate sampling time point, a 1.0 ml sample was removed from the receptor compartment, and replaced with 1.0 ml of fresh buffer.

5. Skin Flux Data Treatment

The quantity of ketorolac tromethamine in each sample was assayed by HPLC analytical methods. In the course of each experiment, the amount of ketorolac tromethamine was corrected after the second time point, as a volume of 1.0 ml of the receiver fluid was removed and replaced with fresh receiver fluid. The cumulative quantity of ketorolac tromethamine in each sampling point was calculated and plotted against the sampling time to give the skin permeation profile. The linear portion of the profile was used to estimate the steady state skin flux by linear regression analysis. Division of the slope of the regression line ($\mu$g/hr) by the permeation area (0.71 cm$^2$) gives the steady state skin flux ($\mu$g/hr/cm$^2$). The acceptance of the skin flux was based on (i) the standard deviation of the replicated experiments (usually n=3), (ii) visual examination of the permeation profiles, and (iii) the standard deviation of each data point for all of the replicated permeation profiles.

6. Ketorolac Release Tests

The procedure for testing release of ketorolac tromethamine from the latex matrix films was the same as that for the skin flux experiments except that no skin was used. The samples were analyzed by HPLC analytical methods. Cumulative amounts were plotted against square root of time to give release rates of $\mu$g/hr$^{1/2}$/cm$^2$.

7. Pretreatment of the Epidermis with Vehicles

In this study, the epidermis was pretreated separately overnight with propylene glycol or PGML. Untreated skin was used as the control. A matrix made of ketorolac tromethamine, PGML, propylene glycol and acrylic AE 2390 was applied to the treated and untreated epidermis in the skin flux experiments.

8. In Vitro Skin Flux from Solution Formulations

The emphasis of this study has been on achieving a target in vitro skin flux of ketorolac tromethamine using safe vehicles and potentially safe acrylic latex matrix formulations. The estimated in vivo skin flux of ketorolac tromethamine from solutions was very high in the presence of propylene glycol and oleic acid, or propylene glycol and lauric acid, using a Rhesus monkey as the animal model (Yu et al., 1988). Therefore, after some suitable solvent vehicles were identified to enhance ketorolac skin flux, the efforts were directed toward the development of ketorolac tromethamine matrices.

9. Monolithic Matrices

After having obtained a very high skin flux of ketorolac from solution formulations (See Table 1), the focus of the investigation has switched to monolithic matrix formulations. There are several solvent combinations which may be used in the development of ketorolac tromethamine matrices. PGML is a proven vehicle for transdermal delivery of active agents, see, e.g., U.S. Pat. No. 4,906,463, and is preferred, in combination with PG, for use as a vehicle in monolithic matrices according to the invention.

Results of an initial screening of ketorolac tromethamine delivery characteristics using a variety of polymers are shown in Table 2. A very low skin flux was obtained when ketorolac tromethamine, PGML and PG were incorporated into either Morstik 607, Gelva 2333, adhesives obtained from Adhesives Research (MA 31, BS02 and AS102), and Flexcryl 1625. However, matrices made with acrylic AE 2390 gave a reasonable flux of 4.7 $\mu$g/hr/cm$^2$, which was reproducible.

The effects of vehicle loading of PGML and PG from 5% to 25% appear to be significant, giving higher skin flux. Much effort was then concentrated on the acrylic AE 2390 polymer system. See Table 3. Loading of both ketorolac tromethamine and PGML has proved to be important in enhancing the skin flux.

Since the target flux of ketorolac (26–40 $\mu$g/hr/cm$^2$) is high depletion of ketorolac from the matrix can become a problem. For a patch of 20 cm$^2$, the amount to be delivered during a 24 hour period ranges from 12.5 to 19.2 mg. To sustain such a high delivery rate, the depletion problem can be met by either of two approaches, namely, (1) loading the matrix with a high concentration of ketorolac tromethamine, or (2) using a thicker matrix.

10. Pretreatment Experiments

The in vitro skin flux results are shown in Table 4. A very high skin flux of 89 $\mu$g/hr/cm$^2$ was obtained in the early part of the permeation profile using skin which was pretreated with PGML.

In transdermal drug delivery from a matrix device, the release of rates of both the drug molecule and the enhancer molecule are very important factors which influence the skin flux. Properly designed solution formulations containing vehicles capable of promoting percutaneous absorption can usually afford a very high skin flux. However, after the vehicles and the drug have been incorporated into a matrix system, the skin flux is often reduced appreciably. It is important to assure an adequate release of both the drug molecules and the enhancer in order to obtain good skin flux.

Although a skin flux of 20 $\mu$g/hr/cm$^2$ was obtained using an acrylic AE 2390 matrix containing 4.5% ketorolac tromethamine, 15% PGML and 15% PG, it is necessary to investigate the ketorolac tromethamine matrix further. In order to eliminate the question of PGML release, we performed a pretreatment experiment using the above matrix formulation, on a control skin and a skin pretreated with PG or PGML. The skin flux for both the control and the skin pretreated with PG are similar, indicating that PG was not acting as an enhancer. However, the skin flux for the skin pretreated with PGML was very high in the early part of the permeation profile. Ketorolac was depleted from the matrix, as evidenced by the plateau of the permeation profile after 10 hours. Also, it is interesting to note that the permeation profile looks like a release profile, indicating that the barrier function of the skin has been diminished greatly.

The solution formulations containing PGML and PG gave a very high skin flux. However, in solutions, owing to direct contact with the skin, PGML could exert fast action on the skin. PG is known to be a good solvent for ketorolac tromethamine (Yu et al., (1988)). When the solution formulations are replaced with the matrix, PGML must first be released from the matrix before it can act on the skin. This release of PGML is very important to skin flux enhancement.

An important point should be mentioned regarding these pretreatment experiments. To obtain a high skin flux, the matrix device must be fabricated in such a way as to be able to release both the drug and the enhancer at a high rate. This will also reduce lag time.

11. Factorial Design of Experiments

Variables such as the ketorolac tromethamine and the PGML loadings in a matrix system contribute greatly to the overall in vitro skin flux of ketorolac. However, other effects from the interaction of variables can occur and can not be revealed with a single variable design. A factorial design of experiments can shown the effect of each variable as well as the effects of variable interactions.

We have made an attempt to use factorial design of experiments to boost the skin flux of ketorolac. Using a general matrix formulation of ketorolac tromethamine. PGML, PG and acrylic AE 2390, and assuming the polymer is a nonvariable, we have studied a design of 3 variables with 2 levels. The results are shown in Table 5. The skin flux for each formulation was done in triplicate and all the standard deviations were within 18%. In general, low loading of ketorolac tromethamine (1.5%), PGML (5%) and PG (5%) gave a low skin flux. However, high loading of ketorolac tromethamine (6%), PGML (25%) and PG (25%) gave a very high skin flux of 38 $\mu$g/hr/cm$^2$. This indicates the importance of all three variables, which is further confirmed by the effects of ketorolac tromethamine, PGML and PG. P is a probability factor, the smaller the value relative to the magnitude of the effect, the more significant the effect. The exclamation mark indicates that the effect associated with it is insignificant. The interactions between KT and PGML, PGML and PG, and among KT, PGML and PG appeared to be insignificant, although there was some interaction between KT and PG. The last interaction effect between KT and PG on the skin flux may be due to the solubility effects of PG on ketorolac tromethamine.

In the future design and development of a transdermal therapeutic system using these materials, optimization of the systems can be done by using the proper proportion of materials to achieve the desired functional properties of the systems (skin flux, wearability, physical testing, and stability testing).

12. Ketorolac Release from Matrices

The release of ketorolac from 9 different types of matrices was investigated. The release rate of ketorolac from silicone 2920, Morstik 607, Gelva 788, MA 31, SB02, and AS102 matrices was very low (Table 6); therefore, these types of matrices were not pursued further. The low release rates may be due to low ketorolac tromethamine loading, since these matrices are lipophilic, and ketorolac tromethamine is a salt. However, two water based polymers, Gelva 2333 and Flex-cryl 1625, showed higher release rates. An increase in PGML or PG loading in the Gelva 2333 matrix did not enhance the release rate. Of all the matrices examined, only the acrylic AE 2390 matrix gave a very high release rate (211 $\mu g/hr^{1/2}/cm^2$). This matrix also a high skin flux.

13. Other Acrylic Polymer Latex Systems

Since acrylic AE 2390 works well for ketorolac tromethamine, we screened additional acrylic polymer latex systems. AE 2616, AE 271, AE 1201 and AE 2390 latexes were used to fabricate matrices containing 1.5% ketorolac tromethamine, 15% PGML and 15% PG. These fabricated matrices were subjected to a ketorolac release and a skin flux study using an acrylic AE 2390 matrix as the control. The release and skin flux results are shown in Table 7. The ketorolac release rates from the systems tested (except AE 1201) are comparable with that form AE 2390. The skin flux of ketorolac from the matrices AE 2390 and AE 2616 are comparable. As the loading of ketorolac was increased from 1.5% to 6% for AE 2616, the flux also increased to 16.1 $\mu g/hr/cm^2$.

When the release rates and the skin flux rates obtained from these matrixes are examined, they cannot be correlated directly, although the general trend is that a higher release rate affords a higher flux.

14. Primary Rabbit Skin Irritation

The means scores for the primary rabbit skin irritation study are shown in Table 8. Because rabbit skin is sensitive during the spring season when these experiments were conducted, the control (mineral oil) shows a mild irritation score of 1.6. PGML and a combination of PGML and PG both show scores similar to that of the mineral oil. The solution formulation of ketorolac in PGML and PG, which gives a very high skin flux of ketorolac, shows a flow score of 2.3. More importantly, the ketorolac monolithic matrix gives a score lower than that of the mineral oil.

EXAMPLE B

Monolithic Matrix Formulations for Delivery of Molsidomine

Further by way of example, monolithic matrices containing molsidomine and having latex matrix formulations according to the invention were made, and their delivery rates were demonstrated in an in vitro model system.

Molsidomine-containing monolithic matrices were made using protocols, and were tested using human cadaver skin, generally as described above for ketorolac-containing monolithic matrices. Two formulations, and the resulting skin flux rates, are as follows.

| Formulations | Skin Flux ($\mu g/hr\text{-}cm^2$) |
|---|---|
| Molsidomine (5%) PGML (5%) PG (5%) AE 2390 (79%) | 6.2 ± 0.1 |
| Molsidomine (5%) PGML (15%) PG (15%) AE 2390 (65%) | 8.1 ± 0.1 |

Other Embodiments

Other embodiments are within the claims.

TABLE 1

IN VITRO SKIN FLUX OF KETOROLAC FROM SOLUTIONS OR SUSPENSIONS

| Formulations | Skin Flux $\mu g/hr/cm^2$ |
|---|---|
| Keto Inj | 11.5 ± 0.9 |
| PGML | |
| KT (90mg) | 25.1 ± 2.7 |
| PGML/PG | |
| 10%/90% | |
| KT (30 mg) | 103.2 ± 2.1 |
| KT (210 mg) | 106.3 ± 2.2 |
| PGML/DDPO4 | |
| 90%/10% | |
| KT (30 mg) | 65.4 ± 10.2 |
| KT(60 mg) | 84 ± 7.5 |
| KT(180 mg) | 144.7 ± 25.6 |
| Oleic acid | |
| KT (30 mg) | 53.0 ± 4.9 |
| Oleic acid/PG | |
| 10%/90% | |
| KT (30 mg) | 48.4 ± 4.9 |
| PGML/Oleic acid/PG | |
| 5%/5%/90% | |
| KT (30 mg) | 64.7 ± 10.8 |
| PGML/Oleic acid/PG | |
| 10%/10%/80% | |
| KT (30 mg) | 68.3 ± 5.1 |
| PGML/Oleic acid/DDPO4/PG | |
| 5%/5%/5%/85% | |
| KT (30 mg) | 458 ± 84.9* |

*Based on early time points
KT = ketorolac tromethamine; PGML = propylene glycol monolaurate; PG = propylene glycol; DDPO4 = dodecylmonophosphate

TABLE 2

IN VITRO KETOROLAC SKIN FLUX FROM MONOLITHIC MATRIX FORMULATIONS

| FORMULATIONS | Skin Flux $\mu g/hr/cm^2$ |
|---|---|
| KT/PGML/PG/Mstk 607 1.5%/4.9%/4.9%/88.6% | 0.8 ± 0.2 |
| KT/PGML/PG/Gelva 2333 1.5%/4.9%/4.9%/88.6% | 0.9 ± 0.2 |
| KT/PGML/PG/MA31 1.5%/4.9%/4.9%/88.6% | 0.3 ± 0.1 |

TABLE 2-continued

IN VITRO KETOROLAC SKIN FLUX FROM MONOLITHIC MATRIX FORMULATIONS

| FORMULATIONS | Skin Flux $\mu g/hr/cm^2$ |
|---|---|
| KT/PGML/PG/BS02 1.5%/4.9%/4.9%/88.6% | 0.5 ± 0.2 |
| KT/PGML/PG/AS102 1.5%/4.9%/4.9%/88.6% | 0.9 ± 0.3 |
| KT/PGML/PG/Gelva 2333 1.5%/9.9%/4.9%/83.7% | 0.6 ± 0.1 |
| KT/PGML/PG/Gelva 2333 1.5%/4.9%/9.9%/83.7% | 0.5 ± 0.1 |
| KT/PGML/PG/Flexcryl 1625 1.5%/4.9%/4.9%/88.6% | 0.2 ± 0.0 |
| KT/PGML/PG/Acrylic AE 2390 4.5%/4.9%/4.9%/86.1% | 4.7 ± 0.3 |

KT = Ketorolac Tromethamine

TABLE 3

VEHICLE LOADING EFFECTS ON THE IN VITRO SKIN FLUX OF KETOROLAC USING MATRICES CONTAINING 4.3% KETOROLAC TROMETHAMINE

| FORMULATIONS | Skin Flux $\mu g/hr/cm^2$ |
|---|---|
| PGML/PG/Acrylic AE 2390 4.8%/4.8%/86% | 4.3 ± 1.1 |
| PGML/PG/Acrylic AE 2390 9.6%/9.6%/76.6% | 9.7 ± 1.1 |
| PGML/PG/Acrylic AE 2390 14.4%/14.4%/67% | 12.2 ± 0.9 |
| PGML/PG/Acrylic AE 2390 23.9%/23.9%/47.9% | 13.6 ± 2.7 |

TABLE 4

IN VITRO SKIN FLUX OF KETOROLAC USING PRETREATED SKINS AND A MATRIX ® CONTAINING 4.3% OF KETOROLAC TROMETHAMINE

| SKINS | Skin Flux $\mu g/hr/cm^2$ |
|---|---|
| Control | 24.2 ± 4.1 |
| Propylene Glycol Pretreated | 26.7 ± 1.6 |
| PGML Pretreated | 89.0 ± 0.2* |

*Based on the early points of the permeation profiles
@ PGML/PG/Acrylic AE 2390 14.4%/14.4%/86.0%

TABLE 5

IN VITRO SKIN FLUX RESULTS FOR A FACTORIAL DESIGN OF EXPERIMENTS

| Exp.No. | KT | PGML | PG | Skin Flux $\mu g/hr/cm^2$ |
|---|---|---|---|---|
| 1 | 1.5% | 5% | 5% | 4.5 ± 0.8 |
| 2 | 6% | 5% | 5% | 7.3 ± 0.5 |
| 3 | 1.5% | 25% | 5% | 15.2 ± 2.0 |
| 4 | 6% | 25% | 5% | 28.3 ± 2.6 |
| 5 | 1.5% | 5% | 25% | 5.7 ± 0.5 |
| 6 | 6% | 5% | 25% | 26.7 ± 2.8 |
| 7 | 1.5% | 25% | 25% | 19.6 ± 0.2 |
| 8 | 6% | 25% | 25% | 38.2 ± 2.3 |
| | | | | p |
| Effect of Ketorolac = 13.88 | | | | 0.1432 |

TABLE 5-continued

IN VITRO SKIN FLUX RESULTS FOR A FACTORIAL DESIGN OF EXPERIMENTS

| Exp.No. | KT | PGML | PG | Skin Flux $\mu g/hr/cm^2$ |
|---|---|---|---|---|
| Effect of PGML = 14.28 | | | | 0.1393 |
| Effect of PG = 8.72 | | | | 0.2222 |
| Effect of Ketorolac/PGML = 2 | | | | 0.6451! |
| Effect of Ketorolac/PG = 5.9 | | | | 0.3132 |
| Effect of PGML/PG = 1.6 | | | | 0.7068! |
| Effect of Ketorolac/PGML/PG = 3.2 | | | | |

TABLE 6

KETOROLAC RELEASE RESULTS FOR MONOLITHIC MATRICES CONTAINING 1.5% KETOROLAC TROMETHAMINE

| Formulations | Release Flux ($\mu g/hr^{1/2}$-$cm^2$) |
|---|---|
| PGML/PG/Sil 2920 4.9%/4.9%/88.6% | low |
| PGML/PG/Mstk 607 4.9%/4.9%/88.6% | 18.5 ± 0.8 |
| PGML/PG/Gelva 788 4.9%/4.9%/88.6% | 9.1 ± 0.2 |
| PGML/PG/Gelva 2333 4.9%/4.9%/88.6% | 34.1 ± 2.7 |
| PGML/PG/MA 31 4.9%/4.9%/88.6% | 9.2 ± 1.2 |
| PGML/PG/SB02 4.9%/4.9%/88.6% | 2.9 ± 0.2 |
| PGML/PG/AS 102 4.9%/4.9%/88.6% | 5.8 ± 2.7 |
| PGML/PG/Gelva 2333 9.9%/4.9%/83.7% | 20.1 ± 1.9 |
| PGML/PG/Gelva 2333 4.9%/9.9%/83.7% | 25.2 ± 1.3 |
| PGML/PG/Flexcryl 1625 4.9%/4.9%/88.6% | 17.8 ± 0.2 |
| KT/PGML/PG/Acrylic 103-90B 4.3%/4.9%/4.9%/88.6% | 211.4 ± 12.9* |

*containing 4.3% ketorolac tromethamine

TABLE 7

KETOROLAC RELEASE AND SKIN FLUX RESULTS USING ACRYLIC LATEXES

| Formulations | Release Flux ($\mu g/hr^{1/2cm2}$) | Skin Flux ($\mu g/hr/cm^2$) |
|---|---|---|
| KT/PGML/PG/AE2390 1.5%/15%/15%/68.5% | 134.3 ± 0.6 | 8.8 ± 0.7 |
| KT/PGML/PG/AE2616 1.5%/15%/15%/68.5% | 94.7 ± 4.9 | 6.8 ± 1.5 |
| KT/PGML/PG/AE2616 6%/20%/15%/59% | | 16.1 ± 1.3 |
| KT/PGML/PG/AE271 1.5%/15%/15%/68.5% | 126.0 ± 0.8 | 5.7 ± 0.6 |
| KT/PGML/PG/AE1201 1.5%/15%/15%/68.5% | 42.8 ± 1.9 | 1.8 ± 0.3 |
| KT/PGML/PG/AE2390 1.5%/15%/15%/68.5% | 142.3 ± 8.1 | 12.4 ± 1.9 |

TABLE 8

PRIMARY RABBIT SKIN IRRITATION STUDY
OF KETOROLAC TROMETHAMINE

| Materials | Mean Scores |
| --- | --- |
| PGML | 1.9 |
| PGML/PG | 1.9 |
| 90%/10% | |
| PGML/PG/KT | 2.3 |
| 10%/84%/6% | |
| KT/PGML/PG/Acrylic AE 2390 | 1.3 |
| 6%/15%/15%/64% | |
| PGML/PG/Acrylic AE 2390 | 1.7 |
| 15%/15%/70% | |
| Drakeol 21 | 1.6 |
| (Mineral Oil) | |

Rating:

| | |
| --- | --- |
| 0 | Non-irritating |
| 0–1.9 | Mildly irritating |
| 2–5.9 | Moderately irrating |
| 6–8 | Severly irritating |

What is claimed is:

1. A laminated device for transdermal administration of molsidomine comprising a backing layer and a matrix layer, the matrix layer comprising:

molsidomine; and an adhesive copolymer composition comprising between 60 and 98 wt % of 2-ethylhexyl acrylate, between 0.1 and 25 wt % of 2-hydroxyethyl methacrylate, and between 0.5 and 10 wt. % of methacrylic acid.

2. The laminated device of claim 1, wherein the adhesive copolymer composition further comprises a vehicle.

3. The laminated device of claim 2, wherein the vehicle is selected from the group consisting of propylene glycol monolaurate and propylene glycol.

4. The laminated device of claim 1, wherein the adhesive copolymer composition further comprises between 0.5 and 10 wt. % of acrylic acid.

5. The laminated device of claim 4, wherein the adhesive copolymer composition further comprises a vehicle.

6. The laminated device of claim 5, wherein the vehicle is selected from the group consisting of propylene glycol monolaurate and propylene glycol.

7. A laminated device for transdermal delivery of molsidomine comprising a backing layer and a matrix layer, the matrix layer comprising:

molsidomine; and an adhesive copolymer composition comprising between 60 and 98 wt % of 2-ethylhexyl acrylate, between 0.1 and 5 wt % of 2-hydroxyethyl methacrylate, between 0.5 and 10 wt. % of methacrylic acid, and between 0.5 and 10 wt. % of acrylic acid; or between 60 and 98 wt. % of 2-ethylhexyl acrylate, between 5 and 25 wt % of 2-hydroxyethyl methacrylate, and between 0.5 and 10 wt. % of methacrylic acid.

8. The laminated device of claim 7, wherein the adhesive copolymer composition further comprises a vehicle.

9. The laminated device of claim 8, wherein the vehicle is selected from the group consisting of propylene glycol monolaurate and propylene glycol.

10. A method for making a matrix composition for use in a laminated device for transdermal delivery of molsidomine, comprising:

combining molsidomine with an adhesive copolymer composition comprising between 60 and 98 wt. % of 2-ethylhexyl acrylate, between 0.1 and 25 wt. % of 2-hydroxyethyl methacrylate, and between 0.5 and 10 wt. % of methacrylic acid.

11. The method of claim 10, wherein the adhesive copolymer composition further comprises a vehicle.

12. The method of claim 11, wherein the vehicle is selected from the group consisting of propylene glycol monolaurate and propylene glycol.

13. The method of claim 10, wherein the adhesive copolymer composition further comprises between 0.5 and 10 wt. % of acrylic acid.

14. The method of claim 13, wherein the adhesive copolymer composition further comprises a vehicle.

15. The method of claim 14, wherein the vehicle is selected from the group consisting of propylene glycol monolaurate and propylene glycol.

16. A method of administering molsidomine to a subject, comprising contacting the laminated device of claim 1 to the subject's skin.

17. A method of administering molsidomine to a subject, comprising contacting the laminated device of claim 3 to the subject's skin.

18. A method of administering molsidomine to a subject, comprising contacting the laminated device of claim 4 to the subject's skin.

19. A method of administering molsidomine to a subject, comprising contacting the laminated device of claim 6 to the subject's skin.

20. A method of administering molsidomine to a subject, comprising contacting the laminated device of claim 7 to the subject's skin.

21. A method of administering molsidomine to a subject, comprising contacting the laminated device of claim 9 to the subject's skin.

* * * * *